(12) United States Patent
Kanaoka et al.

(10) Patent No.: US 7,078,121 B2
(45) Date of Patent: Jul. 18, 2006

(54) AROMATIC SULFONATE DERIVATIVE, POLYARYLENE, SULFONATED POLYARYLENE AND PRODUCTION METHOD THEREOF, MACROMOLECULAR SOLID ELECTROLYTE, AND PROTON CONDUCTIVE MEMBRANE

(75) Inventors: Nagayuki Kanaoka, Wako (JP); Masaru Iguchi, Wako (JP); Naoki Mitsuta, Wako (JP); Hiroshi Soma, Wako (JP); Toshihiro Ohtsuki, Tokyo (JP)

(73) Assignees: JSR Corporation, Tokyo (JP); Honda Motor Co., Ltd., Tokyo (JP)

( * ) Notice: Subject to any disclaimer, the term of this patent is extended or adjusted under 35 U.S.C. 154(b) by 0 days.

(21) Appl. No.: 10/734,194

(22) Filed: Dec. 15, 2003

(65) Prior Publication Data

US 2004/0126639 A1    Jul. 1, 2004

(30) Foreign Application Priority Data

Dec. 18, 2002    (JP)    .............................. 2002-367042

(51) Int. Cl.
*H01M 8/10*   (2006.01)
*C08G 61/10*  (2006.01)
*C08G 61/12*  (2006.01)
*C08L 65/00*  (2006.01)
*C08L 65/02*  (2006.01)

(52) U.S. Cl. ........................ 429/33; 528/391; 528/397; 528/125; 528/171; 528/499; 429/30

(58) Field of Classification Search ................ 528/391, 528/499, 397, 125, 171; 429/33
See application file for complete search history.

(56) References Cited

U.S. PATENT DOCUMENTS 5,403,675 A    4/1995    Ogata et al.

FOREIGN PATENT DOCUMENTS

| EP | 1 138 712 A2 | 10/2001 |
|----|--------------|---------|
| EP | 1 245 554 A1 | 10/2002 |
| EP | 1 245 555 A1 | 10/2002 |

*Primary Examiner*—Duc Truong
(74) *Attorney, Agent, or Firm*—Arent Fox PLLC

(57) ABSTRACT

Described herein is a production method of sulfonated polyarylene that is safe and enables easy control of the amount and position of sulfonic groups introduced in the polymer. The sulfonated polyarylene is also disclosed. The invention further provides a polyarylene and an aromatic sulfonate derivative that are suitably employed in the above production method. Also provided are a macromolecular solid electrolyte that comprises the sulfonated polyarylene, and a proton conductive membrane.

The aromatic sulfonate derivative has the following formula (1):

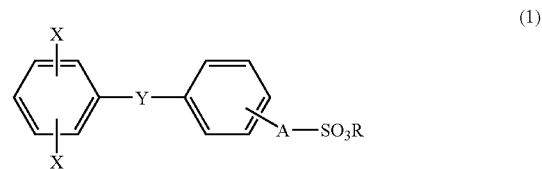

(1)

wherein X is a halogen atom other than fluorine, a —$OSO_2CH_3$ group or a —$OSO_2CF_3$ group; Y is a divalent organic group; A is —$(CH_2)_m$— or —$(CF_2)_m$— (wherein m is an integer of 1 to 10); and R is a $C_{4-20}$ hydrocarbon group.

The production method of sulfonated polyarylene comprises coupling polymerization of an aromatic compound that includes at least the aromatic sulfonate derivative of the formula (1) and hydrolysis of the resultant polyarylene.

3 Claims, No Drawings

AROMATIC SULFONATE DERIVATIVE, POLYARYLENE, SULFONATED POLYARYLENE AND PRODUCTION METHOD THEREOF, MACROMOLECULAR SOLID ELECTROLYTE, AND PROTON CONDUCTIVE MEMBRANE

FIELD OF THE INVENTION

The present invention relates to a novel aromatic sulfonate derivative. It also relates to a polyarylene containing structural units that are derived from said ester compound. Further, the invention relates to a sulfonated polyarylene obtained by hydrolysis of the polyarylene, and to a production method thereof. And the invention relates to a macromolecular solid electrolyte comprising the sulfonated polyarylene, and to a proton conductive membrane containing the electrolyte.

BACKGROUND OF THE INVENTION

Recently, electrolytes have a high tendency to be used in the form of solid rather than the conventional form of (aqueous) solution. This is because firstly those solid electrolytes have good processability so that they can be easily applied in electric and electronic components, and secondly there are trends for reduction of weight, thickness, length and size of such components and further for power saving.

Proton conductive materials, both inorganic and organic, are known in the art. However, inorganic proton conductive materials, such as uranyl phosphate hydrates, come with many difficulties when superposed as a conductive layer onto a substrate or an electrode. For example, sufficient contact cannot be achieved in the interface between the conductive layer and the substrate, etc.

On the other hand, organic proton conductive compounds may be exemplified with polymers that belong to the cation exchange resins, e.g. sulfonated vinyl polymers such as polystyrene sulfonic acid; perfluoroalkylsulfonic acid polymers, which are typically represented by Nafion® (Du Pont Kabushiki kaisha); perfluoroalkylcarboxylic acid polymers; and heat resistant polymers, including polybenzimidazole and polyether ether ketone, in which sulfonic or phosphoric groups have been introduced (Polymer Preprints, Japan, Vol. 42, No. 7, p. 2490–2492 (1993), Polymer Preprints, Japan, Vol. 43, No. 3, p. 735–736 (1994), Polymer Preprints, Japan, Vol. 42, No. 3, p. 730 (1993)).

Sulfonated polyarylenes also are known as proton conductive materials; they are generally obtained by polymerizing an aromatic compound and reacting the resultant polymer with a sulfonating agent to thereby introduce a sulfonic group into the polymer.

In the current sulfonation methods, the sulfonating agents, including concentrated sulfuric acid, fuming sulfuric acid and chlorosulfuric acid, have to be used in large amounts. This increases production risks and limits the variety of available plant materials. Further, cumbersome work is required to carry out a wastewater treatment after the polymer has been recovered. Also, it is difficult with the conventional sulfonation methods to control the amount and position of sulfonic groups introduced into the polymer.

OBJECTS OF THE INVENTION

The present invention aims to solve these prior art problems. Accordingly, it is an object of the invention to provide a production method of sulfonated polyarylene that involves no sulfonating agents, can reduce the work for the post-production waste treatment, and enables easy control of the amount and position of sulfonic groups to be introduced in the polymer. It is another object of the invention to provide a sulfonated polyarylene obtained by the above method. It is a further object to provide a novel aromatic sulfonate derivative and a novel polyarylene that are suitably used in the production of the sulfonated polyarylene.

It is a still further object of the invention to provide a macromolecular solid electrolyte that comprises the sulfonated polyarylene, and a proton conductive membrane that includes the macromolecular solid electrolyte.

SUMMARY OF THE INVENTION

To achieve the above objects, the invention provides the following.

(1) An aromatic sulfonate derivative represented by the formula (1):

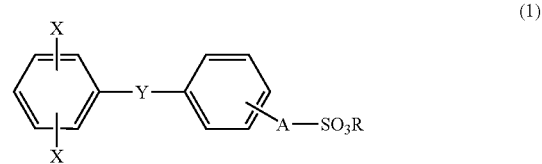

(1)

wherein X is a halogen atom other than fluorine, a $-OSO_3CH_3$ group or a $-OSO_3CF_3$ group; Y is a divalent organic group; A is $-(CH_2)_m-$ or $-(CF_2)_m-$ (wherein m is an integer of 1 to 10); and R is a $C_{4-20}$ hydrocarbon group.

(2) The aromatic sulfonate derivative as described in (1), wherein Y in the formula (1) is an electron-attracting group.

(3) The aromatic sulfonate derivative as described in (1), wherein Y in the formula (1) is $-CO-$ or $-SO_2-$ group.

(4) A polyarylene comprising structural units derived from an aromatic compound, wherein at least part of the structural units are represented by the formula (1'):

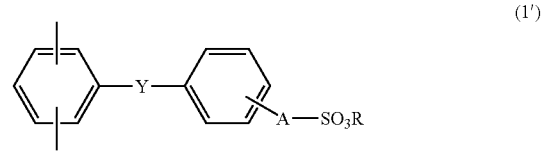

(1')

wherein Y is a divalent organic group; A is $-(CH_2)_m-$ or $-(CF_2)_m-$ (wherein m is an integer of 1 to 10); and R is a $C_{4-20}$ hydrocarbon group.

(5) The polyarylene as described in (4), which comprises 0.5–100 mol % structural units represented by the formula (1') and 0–99.5 mol % structural units represented by the following formula (A'):

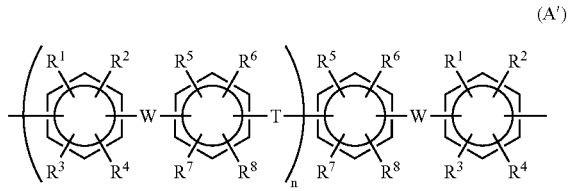

(A')

wherein $R^1$ to $R^8$, which may be the same or different, are independently at least one atom or group selected from the group consisting of a hydrogen atom, a fluorine atom, and alkyl, fluorine-substituted alkyl, allyl and aryl groups; W is a divalent electron-attracting group; and T is a divalent organic group.

(6) A sulfonated polyarylene obtained by hydrolysis of the polyarylene described in (4) or (5).

(7) A production method of sulfonated polyarylene, comprising coupling polymerization of an aromatic compound that contains at least the aromatic sulfonate derivative described in (1) and hydrolysis of the resultant polyarylene.

(8) A macromolecular solid electrolyte comprising the sulfonated polyarylene described in (6).

(9) A proton conductive membrane for fuel cells that contains the macromolecular solid electrolyte described in (8).

DESCRIPTION OF THE PREFERRED EMBODIMENTS

Hereinafter, the aromatic sulfonate derivative, polyarylene, sulfonated polyarylene and production method thereof, macromolecular solid electrolyte and proton conductive membrane according to the invention will be described in detail.

(Aromatic Sulfonate Derivative)

The aromatic sulfonate derivative of the invention has the formula (1):

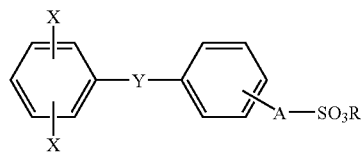

(1)

X is a halogen atom other than fluorine (i.e. chlorine, bromine or iodine), a —$OSO_3CH_3$ group or a —$OSO_3CF_3$ group.

Y is a divalent organic group. Examples thereof include electron-attracting groups such as —CO—, —CONH—, —$(CF_2)_p$— (wherein p is an integer of 1 to 10), —$C(CF_3)_2$—, —COO—, —SO—, —$SO_2$— and the like; and electron-donating groups such as —O—, —S—, —CH=CH—, —C≡C— and groups having the following formulae:

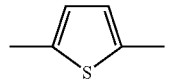 and 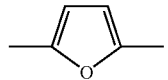

The electron-attracting groups, particularly —CO— and —$SO_2$—, are preferable as Y since their use leads to an enhanced acid strength of the sulfonated polyarylene and a higher temperature for elimination of the sulfonic group.

The electron-attracting group may be defined as a group with a Hammett substituent constant of not less than 0.06 at the m-position of a phenyl group and not less than 0.01 at the p-position.

A is —$(CH_2)_m$— or —$(CF_2)_m$— (wherein m is an integer of 1 to 10, and preferably 1 to 8).

R is a $C_{4-20}$ hydrocarbon group selected from, for example, linear hydrocarbon groups, branched hydrocarbon groups, alicyclic hydrocarbon groups and hydrocarbon groups with five-membered heterorings. Specific examples include tert-butyl, iso-butyl, n-butyl, sec-butyl, neopentyl, cyclopentyl, hexyl, cyclohexyl, cyclopentylmethyl, cyclohexylmethyl, adamantyl, adamantylmethyl, 2-ethylhexyl, bicyclo(2.2.1)heptyl, bicyclo(2.2.1)heptylmethyl, tetrahydrofurfuryl, 2-methylbutyl, 3,3-dimethyl-2,4-dioxolanemethyl, cyclohexylmethyl, adamantylmethyl and bicyclo(2.2.1)heptylmethyl groups. Of these, the neopentyl, tetrahydrofurfuryl, cyclopentylmethyl, cyclohexylmethyl, adamantylmethyl and bicyclo(2.2.1)heptylmethyl groups are preferred, and the neopentyl group is more preferred.

The aromatic sulfonate derivative having the formula (1) may be exemplified with the following compounds:

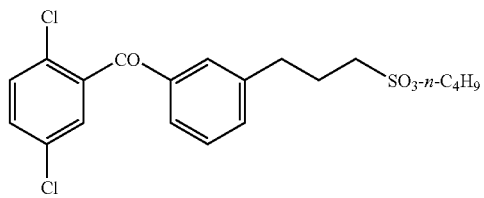

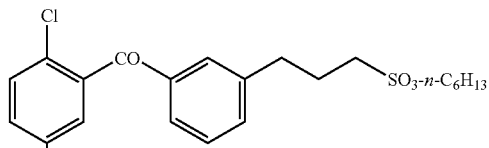

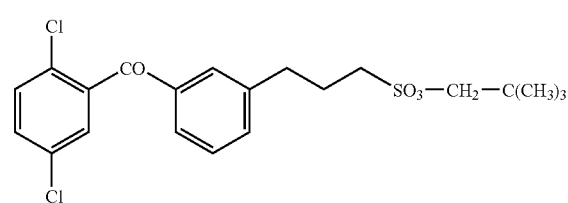

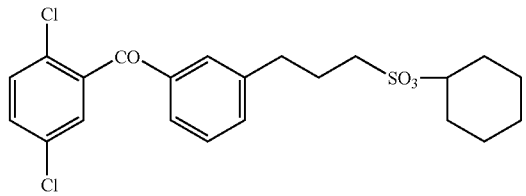

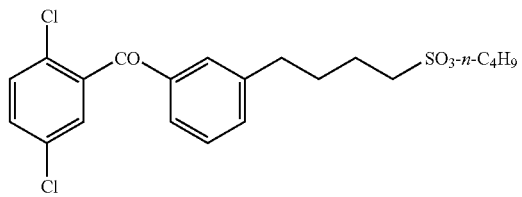

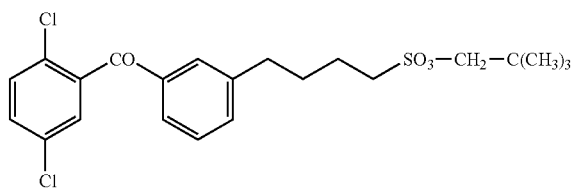

-continued

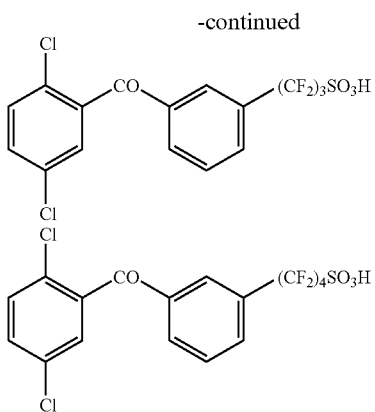

In the compounds illustrated as the aromatic sulfonate derivative of the formula (1), it is also likely that the chlorine atom is replaced by a bromine atom, the —CO— group is replaced by a —SO$_2$— group, or these two replacements occur at the same time.

The ester groups in the above aromatic sulfonate derivatives are preferably derived from a primary alcohol, and the β carbon atoms are preferably tertiary or quaternary. More preferably, the ester groups are derived from a primary alcohol and the β carbon atoms are quaternary. When these two conditions are satisfied, an excellent stability will be obtained during the polymerization and no inhibited polymerization or crosslinking will result from the formation of sulfonic acids by deesterification.

(Synthesis Method of the Aromatic Sulfonate Derivative)

The aromatic sulfonate derivative according to the invention may be synthesized by introducing the sulfo(fluoro)alkyl group —A—SO$_3$R into an aromatic hydrocarbon represented by the formula (2):

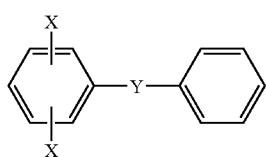

(2)

wherein X and Y are as defined in the formula (1). Herein sulfo(fluoro)alkyl denotes either sulfoalkyl or sulfofluoroalkyl.

The method for introducing the sulfo(fluoro)alkyl group —A—SO$_3$R into the aromatic hydrocarbon polymer, i.e. the sulfo(fluoro)alkylation method is not particularly limited. Specifically, J. Amer. Chem. Soc., 76, 5357–5360 (1954) describes an exemplary process, in which the sulfo(fluoro)alkyl group is introduced into an aromatic ring with use of sultone.

The sulfo(fluoro)alkylation is also possible by a series of steps in which the hydrogen in the aromatic ring is substituted with lithium, which is thereafter substituted with a halogeno(fluoro)alkyl group using dihalogeno(fluoro)alkane, and the halogeno(fluoro)alkyl group is converted into the sulfo(fluoro)alkyl group; or by a series of steps in which a halogenobutyl group is introduced using a tetramethylene halogenium ion and the halogen is converted into the sulfonic group.

(Sulfonated Polyarylene)

The sulfonated polyarylene of the invention may be obtained by hydrolyzing a polyarylene that results from:

(co)polymerization of at least one monomer selected from the aromatic sulfonate derivatives of the formula (1), or copolymerization of at least one such monomer of the formula (1) with one or more other aromatic monomers, preferably with one or more monomers selected from the compounds of the following formula (A):

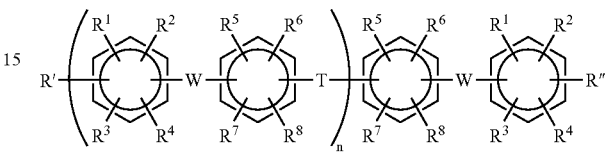

(A)

In the formula (A), R' and R", which may be the same or different, are independently a halogen atom other than fluorine or a —OSO$_2$Z group (where Z is an alkyl group, a fluorine-substituted alkyl group or an aryl group).

Exemplary groups indicated by Z include methyl and ethyl for the alkyl groups; trifluoromethyl for the fluorine-substituted alkyl groups; and phenyl and p-tolyl for the aryl groups.

$R^1$ to $R^8$, which may be the same or different, are independently at least one atom or group selected from the group consisting of a hydrogen atom, a fluorine atom, and alkyl, fluorine-substituted alkyl, allyl and aryl groups.

Examples of the alkyl groups include methyl, ethyl, propyl, butyl, amyl and hexyl. Of these, methyl, ethyl, etc. are preferred.

Examples of the fluorine-substituted alkyl groups include trifluoromethyl, perfluoroethyl, perfluoropropyl, perfluorobutyl, perfluoropentyl and perfluorohexyl. Of these, trifluoromethyl, pentafluoroethyl, etc. are preferred.

Examples of the allyl groups include propenyl.

Examples of the aryl groups include phenyl and pentafluorophenyl.

W denotes a divalent, electron-attracting group, which may be selected from the electron-attracting groups listed hereinabove.

T is a divalent organic group that is capable of electron attraction or donation. Hereat, the electron attracting or donating group may be any one selected from the same ones as given above.

In the above formula, n is 0 or a positive integer of up to 100, preferably up to 80.

Exemplary compounds having the formula (A) in which n is 0 include 4,4'-dichlorobenzophenone, 4,4'-dichlorobenzanilide, bis(chlorophenyl)difluoromethane, 2,2-bis(4-chlorophenyl)hexafluoropropane, 4-chlorobenzoic acid-4-chlorophenyl, bis(4-chlorophenyl)sulfoxide, bis(4-chlorophenyl)sulfone, corresponding compounds to the above compounds except that the chlorine atom is replaced with a bromine or an iodine atom, and corresponding compounds to the above compounds except that at least one halogen atom present at the 4-position shifts to the 3-position.

Exemplary compounds having the formula (A) in which n is 1 include 4,4'-bis(4-chlorobenzoyl)diphenyl ether, 4,4'-bis(4-chlorobenzoylamino)diphenyl ether, 4,4'-bis(4-chlorophenylsulfonyl)diphenyl ether, 4,4'-bis(4-chlorophenyl) diphenyl ether dicarboxylate, 4,4'-bis((4-chlorophenyl)-1,1, 1,3,3,3-hexafluoropropyl) diphenyl ether, 4,4'-bis((4-chlorophenyl)tetrafluoroethyl) diphenyl ether, corresponding compounds to the above compounds except that the chlorine atom is replaced with a bromine or an iodine atom, corresponding compounds to the above compounds except that the halogen substitution is present at the 3-position in place of the 4-position, and corresponding compounds to the above compounds except that at least one substituent group at the 4-position of diphenyl ether shifts to the 3-position.

Also available as the compounds of the formula (A) are 2,2-bis(4-(4-(4-chlorobenzoyl)phenoxy)phenyl)-1,1,1,3,3,3-hexafluoropropane, bis(4-(4-(4-chlorobenzoyl) phenoxy) phenyl)sulfone, and compounds represented by the following formulae:

The polar solvents used herein include N-methyl-2-pyrrolidone, N,N-dimethylacetamide, sulfolane, diphenyl sulfone and dimethyl sulfoxide.

The alkali metal, etc. will be generally used in rather slight excess based on the hydroxyl groups of the bisphenol, for example usually 1.1 to 2 times, and preferably 1.2 to 1.5 times equivalent amount.

Thereafter, the alkali metal salt of bisphenol is reacted with a halogen-substituted, e.g. fluorine- or chlorine-substituted, aromatic dihalide compound that has been activated by the electron-attracting groups, in the presence of a solvent which can form an azeotropic mixture with water, such as benzene, toluene, xylene, hexane, cyclohexane, octane, chlorobenzene, dioxane, tetrahydrofuran, anisole or phenetole. Examples of the above aromatic dihalide compound

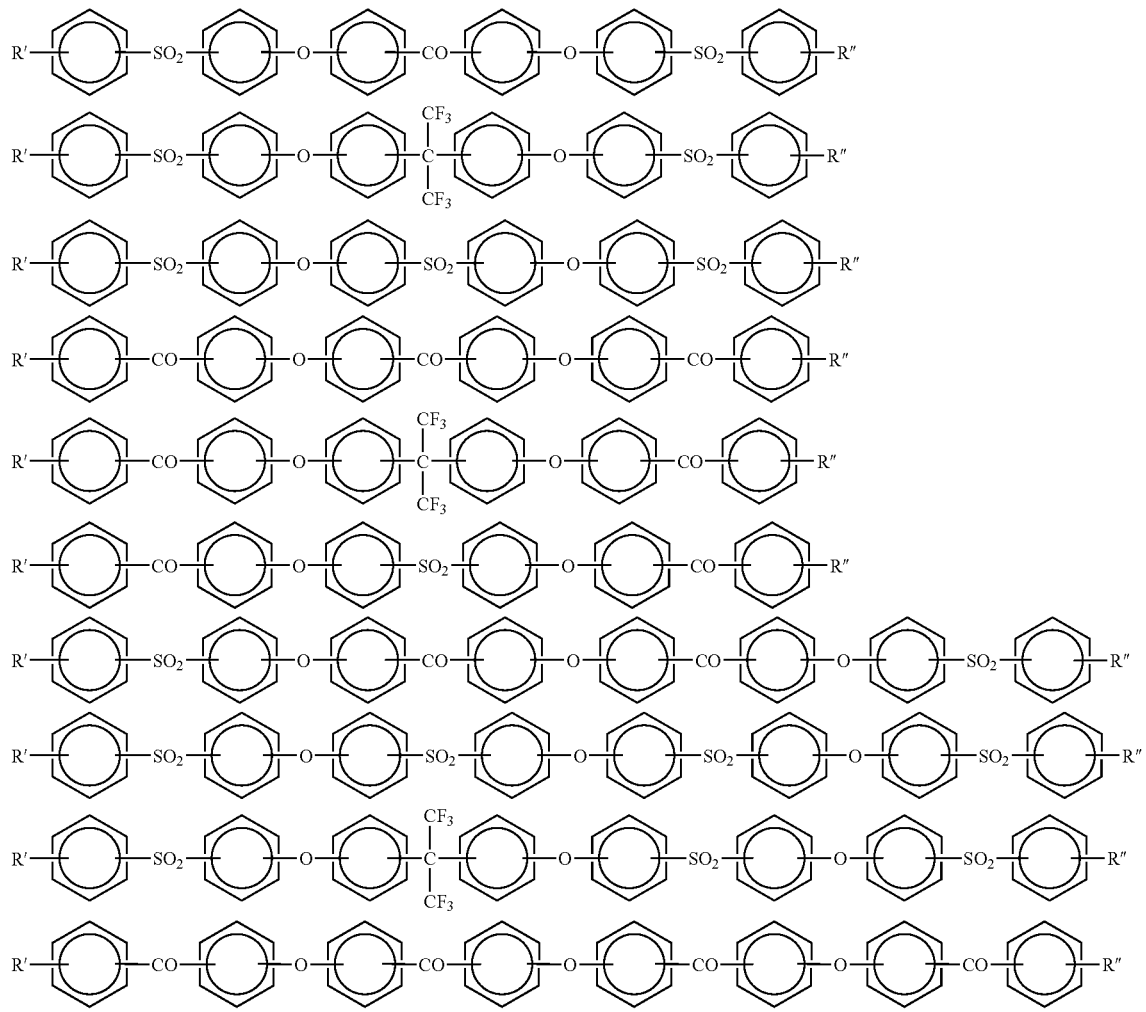

For example, the compound having the formula (A) may be synthesized by the following process.

First, bisphenols combined together by the electron-attracting group will be converted into a corresponding alkali metal salt of bisphenol. To make such conversion, an alkali metal such as lithium, sodium or potassium, or an alkali metal compound such as an alkali metal hydride, an alkali metal hydroxide or an alkali metal carbonate, is added to the bisphenols in a polar solvent with a high dielectric constant.

include 4,4'-difluorobenzophenone, 4,4'-dichlorobenzophenone, 4,4'-chlorofluorobenzophenone, bis(4-chlorophenyl) sulfone, bis(4-fluorophenyl)sulfone, 4-fluorophenyl-4'-chlorophenylsulfone, bis(3-nitro-4-chlorophenyl)sulfone, 2,6-dichlorobenzonitrile, 2,6-difluorobenzonitrile, hexafluorobenzene, decafluorobiphenyl, 2,5-difluorobenzophenone and 1,3-bis(4-chlorobenzoyl)benzene. From the viewpoint of reactivity, the aromatic dihalide compound is desirably a fluorine compound. But taking the subsequent aromatic coupling reaction into account, the aromatic nucleophilic substitution reaction should be designed to occur so as to yield a molecule terminated with a chlorine atom at its end(s). The active aromatic dihalide compound may be used in an amount 2 to 4 molar times, and preferably 2.2 to 2.8 molar times the amount of the bisphenol. The reaction temperature is in the range of 60 to 300° C., and preferably 80 to 250° C. The reaction time is in the range of 15 minutes to 100 hours, and preferably 1 to 24 hours. Optimally, the active aromatic dihalide compound is a chlorofluoro compound of the formula given hereinbelow that has two halogen atoms different in reactivity each other. The use of this compound is advantageous in that the fluorine atom will preferentially undergo the nucleophilic substitution reaction with phenoxide so that the objective chlorine-terminated active compound may be obtained:

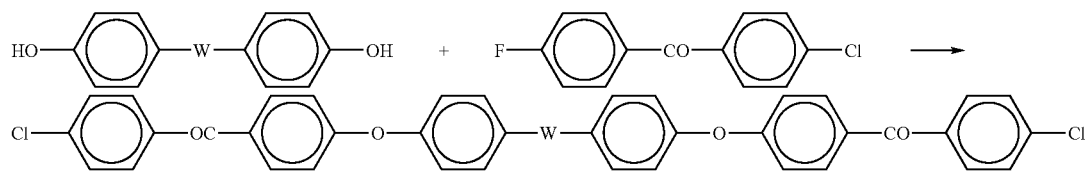

wherein W is as defined in the formula (A).

JP-A-2(1990)/159 discloses another method of the synthesis, in which the nucleophilic substitution reaction is carried out combined with an electrophilic substitution reaction to synthesize the objective flexible compound that comprises the electron-attracting and electron-donating groups.

Specifically, the aromatic bis-halide activated by the electron-attracting group, such as bis(4-chlorophenyl)sulfone, is subjected to the nucleophilic substitution reaction with phenol; the resulting bis-phenoxy substituted compound is subjected to Friedel-Crafts reaction with, for example, 4-chlorobenzoyl chloride to obtain the objective compound. Hereat, any of the above-listed compounds may be used as the aromatic bis-halide activated by the electron-attracting group. The phenol compound may be substituted, but is preferably unsubstituted from the viewpoints of heat resistance and flexibility. When substituted, the substituted phenol compound is preferably an alkali metal salt. Any of the alkali metal compounds listed above may be used for the substitution reaction. The alkali metal compound is used in an amount 1.2 to 2 molar times the amount of the phenol. In the reaction, the aforesaid polar solvent or the azeotropic solvent with water may be employed. To obtain the objective compound, the bis-phenoxy compound is reacted with chlorobenzoyl chloride as an acylating agent in the presence of an activator for the Friedel-Crafts reaction, e.g. Lewis acid such as aluminum chloride, boron trifluoride or zinc chloride. The chlorobenzoyl chloride is used in an amount 2 to 4 molar times, and preferably 2.2 to 3 molar times the amount of the bis-phenoxy compound. The Friedel-Crafts reaction activator is used in 1.1 to 2 times equivalent amount based on 1 mol of the active halide compound, such as an acylating agent chlorobenzoic acid. The reaction time is in the range of 15 minutes to 10 hours, and the reaction temperature in the range of −20 to 80° C. As a solvent, chlorobenzene, nitrobenzene or the like that is inactive in the Friedel-crafts reaction may be used.

The polymer having the formula (A) in which n is 2 or more may be synthesized through the polymerization also in accordance with the above-mentioned method. For example, an alkali metal salt of bisphenol such as 2,2-bis(4-hydroxyphenyl)-1,1,1,3,3,3-hexafluoropropane, 2,2-bis(4-hydroxyphenyl)ketone or 2,2-bis(4-hydroxyphenyl) sulfone, which has resulted from the combination of a bisphenol that can supply ether oxygen as the electron-donating group T with the electron-attracting group W of >C=O, —SO$_2$— and/or >C(CF$_3$)$_2$, is subjected to a substitution reaction with an excess of the activated aromatic halogen compound such as 4,4-dichlorobenzophenone or bis(4-chlorophenyl)sulfone, in the presence of a polar solvent such as N-methyl-2-pyrrolidone, N,N-dimethylacetamide or sulfolane.

Examples of such polymers include the compounds having the following formulae:

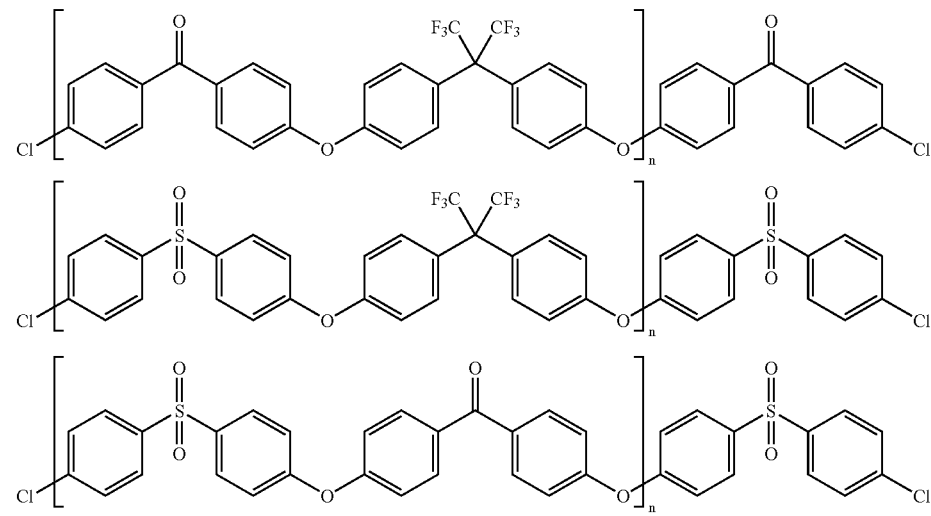

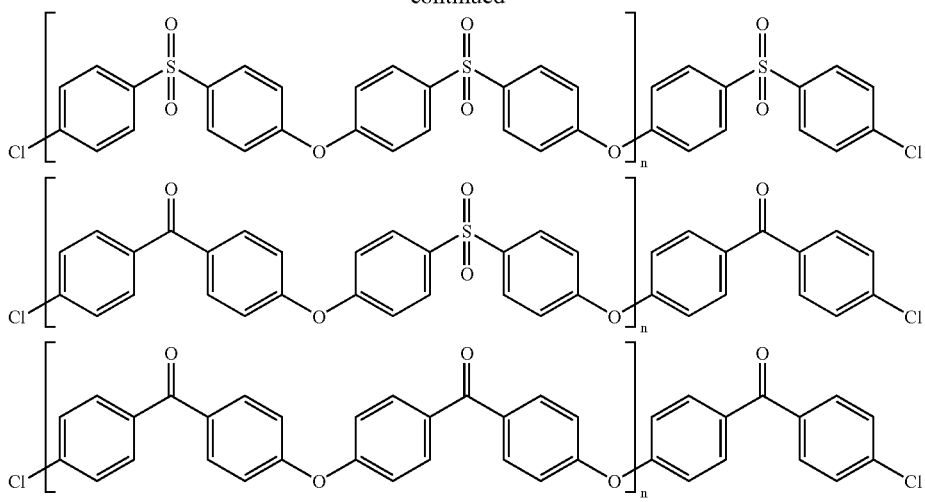

In these formulae, n is 2 or more, and preferably from 2 to 100.

The polyarylene according to the invention comprises structural units derived from an aromatic compound; at least part of the structural units are represented by the formula (1'):

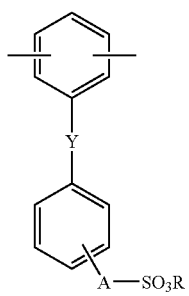

(1')

wherein Y, A and R are as defined in the formula (1).

The other part of the structural units of the polyarylene will be represented by the following formula (A'):

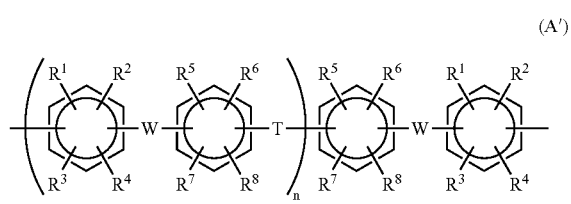

(A')

wherein $R^1$ to $R^8$, W, T and n are as defined in the formula (A)

Preferably, the polyarylene will contain the structural units (1') in an amount of, although not particularly limited thereto, from 0.5 to 100 mol %, and more preferably from 10 to 99.999 mol %. The content of the structural units (A') will be preferably 0 to 99.5 mol %, and more preferably 0.001 to 90 mol % of the polyarylene.

(Synthesis of the Polyarylene)

To synthesize the polyarylene, one or more monomers selected from the aromatic sulfonate derivatives of the formula (1) are reacted in the presence of a catalyst. Alternatively, those one or more aromatic sulfonate derivatives, 0.5 to 100 mol %, preferably 10 to 99.999 mol %, may be reacted in the presence of a catalyst with one or more monomers, 0 to 99.5 mol %, preferably 0.001 to 90 mol %, selected from other aromatic monomers, preferably from the compounds having the formula (A). The catalyst used herein is a catalyst system containing a transition metal compound.

This catalyst system essentially contains (1) a transition metal salt and a compound which functions as a ligand (referred to as "ligand component" hereinafter), or a transition metal complex (including a copper salt) to which a ligand(s) has been coordinated, and (2) a reducing agent. A "salt" may be added to increase the polymerization rate.

Examples of the transition metal salt include nickel compounds such as nickel chloride, nickel bromide, nickel iodide and nickel acetylacetonate; palladium compounds such as palladium chloride, palladium bromide and palladium iodide; iron compounds such as iron chloride, iron bromide and iron iodide; and cobalt compounds such as cobalt chloride, cobalt bromide and cobalt iodide. Of these, nickel chloride, nickel bromide, etc. are particularly preferred.

Examples of the ligand component include triphenylphosphine, 2,2'-bipyridine, 1,5-cyclooctadiene and 1,3-bis(diphenylphosphino)propane. Of these, triphenylphosphine and 2,2'-bipyridine are preferred. The ligand components may be used singly or in combination of two or more kinds.

Examples of the transition metal complex with coordinated ligands include
nickel chloride-bis (triphenylphosphine),
nickel bromide-bis(triphenylphosphine),
nickel iodide-bis(triphenylphosphine),
nickel nitrate-bis(triphenylphosphine),
nickel chloride(2,2'-bipyridine),
nickel bromide(2,2'-bipyridine),
nickel iodide(2,2'-bipyridine),
nickel nitrate(2,2'-bipyridine),
bis(1,5-cyclooctadiene)nickel,
tetrakis(triphenylphosphine)nickel,
tetrakis(triphenylphosphite)nickel and tetrakis(triphenylphosphine)palladium. Of these, nickel chloride-bis(triphenylphosphine) and nickel chloride(2, 2'-bipyridine) are preferred.

Examples of the reducing agent employable in the aforesaid catalyst system include iron, zinc, manganese, aluminum, magnesium, sodium, calcium and the like. Of these, zinc, magnesium and manganese are preferable. These reducing agents may be used in a more activated form brought about by contact with an acid, e.g. an organic acid.

Examples of the "salt" employable in the catalyst system include sodium compounds such as sodium fluoride, sodium chloride, sodium bromide, sodium iodide and sodium sulfate; potassium compounds such as potassium fluoride, potassium chloride, potassium bromide, potassium iodide and potassium sulfate; and ammonium compounds such as tetraethylammonium fluoride, tetraethylammonium chloride, tetraethylammonium bromide, tetraethylammonium iodide and tetraethylammonium sulfate. Of these, sodium bromide, sodium iodide, potassium bromide, tetraethylammonium bromide and tetraethylammonium iodide are preferred.

With respect to the proportion of the above components, the transition metal salt or the transition metal complex will be used usually in an amount of 0.0001 to 10 mol, and preferably 0.01 to 0.5 mol based on 1 mol of the total monomers. Any amounts less than 0.0001 mol can lead to incomplete polymerization. Contrary, the amount over 10 mol may result in a lowered molecular weight of the polyarylene.

When the catalyst system contains the transition metal salt and the ligand component, the ligand component will be used usually in an amount of 0.1 to 100 mol, and preferably 1 to 10 mol based on 1 mol of the transition metal salt. If this amount falls less than 0.1 mol, the catalytic activity may become insufficient. On the other hand, the amount exceeding 100 mol may result in a lowered molecular weight of the polyarylene.

The amount of the reducing agent will be usually in the range of 0.1 to 100 mol, and preferably 1 to 10 mol based on 1 mol of the total monomers. The amount being less than 0.1 mol, the polymerization may not proceed adequately. Contrary, the amount exceeding 100 mol may make the purification of the resulting polymer more difficult.

When the "salt" is used, the amount thereof will be usually 0.001 to 100 mol, and preferably 0.01 to 1 mol based on 1 mol of the total monomers. The salt added in amounts less than 0.001 mol may not be able to produce sufficient effects of increasing the polymerization rate. Contrary, the amount thereof exceeding 100 mol may result in difficult purification of the resulting polymer.

Exemplary solvents usable in the above polymerization include tetrahydrofuran, cyclohexanone, dimethyl sulfoxide, N,N-dimethylformamide, N,N-dimethylacetamide, N-methyl-2-pyrrolidone, γ-butyrolactone, sulfolane, γ-butyrolactam, dimethylimidazolidinone and tetramethylurea. Of these, tetrahydrofuran, N,N-dimethylformamide, N,N-dimethylacetamide and N-methyl-2-pyrrolidone are preferred. These polymerization solvents are desirably used after sufficiently dried.

The concentration of the total monomers in the polymerization solvent will be usually in the range of 1 to 90 wt %, and preferably 5 to 40 wt %.

The polymerization temperature will be usually 0 to 200° C., and preferably 50 to 120° C. The polymerization time will be generally 0.5 to 100 hours, and preferably 1 to 40 hours.

The (co)polymerization of one or more monomers selected from the aromatic sulfonate derivatives of the formula (1), or the copolymerization of those one or more aromatic sulfonate derivatives with at least one compound having the formula (A), produces a polymerization solution that contains the polyarylene.

The thus-obtained polyarylene will have a weight-average molecular weight in terms of polystyrene of 10,000 to 1,000,000, and preferably 20,000 to 800,000 as measured by a gel permeation chromatography (GPC).

(Sulfonated Polyarylene)

The above polyarylene will be subjected to a hydrolysis to convert the sulfonate ester group $-SO_3R$ of the structural units (1') into the sulfonic acid group $-SO_3H$. The sulfonated polyarylene of the invention may be thus prepared.

For example, the hydrolysis may be accomplished by any of the following methods:

(1) Add the polyarylene to an excess of water or an alcohol that contains hydrochloric acid in a small quantity, and stir the mixture for at least 5 minutes;

(2) React the polyarylene in trifluoroacetic acid at about 80 to 120° C. and for about 5 to 10 hours;

(3) React the polyarylene in a solution, e.g. N-methylpyrrolidone, that contains lithium bromide in a 1 to 3 molar times amount based on 1 mol of the sulfonate group $-SO_3R$ of the polyarylene, at about 80 to 150° C. and for about 3 to 10 hours, and add the hydrochloric acid to the reaction product.

The sulfonated polyarylene thus obtained will contain the sulfonic group in an amount of 0.5 to 3 meq/g, and preferably 0.8 to 2.8 meq/g. If the sulfonic group has a proportion below 0.5 meq/g, the proton conductivity will become poor. In contrast, the amount thereof over 3 meq/g will cause the polymer to have so high a hydrophilicity as to make it less durable or, even worse, soluble in water or hot water.

The above amount of sulfonic group may be readily controlled by altering the proportion between the aromatic sulfonate derivative and the compound (A), or by changing the type or combination of the monomers.

The structure of the sulfonated polyarylene may be determined based on its infrared absorption spectrum, for example the C—O—C absorption at 1230 to 1250 $cm^{-1}$ or the C=O absorption at 1640 to 1660 $cm^{-1}$. The confirmation is also possible from the peak of aromatic protons at 6.8–8.0 ppm in the nuclear magnetic resonance spectrum ($^1$H-NMR).

In the polyarylene of the invention, the conversion rate for the sulfonate groups $-SO_3R$ into the sulfonic acid groups $-SO_3H$ is preferably 90% or more.

(Macromolecular Solid Electrolyte)

The macromolecular solid electrolyte according to the invention comprises the above-described sulfonated polyarylene.

The macromolecular solid electrolyte can find its uses in electrolytes for primary and secondary batteries, and as proton conductive membranes for fuel cells, display elements, sensors, signaling media and solid condensers, and as other ion exchange membranes.

(Proton Conductive Membrane)

The proton conductive membrane of the invention comprises the sulfonated polyarylene described above. In preparing the proton conductive membrane from the sulfonated polyarylene, it is optionally possible to add an inorganic acid such as sulfuric acid or phosphoric acid; an organic acid containing carboxylic acid; or an appropriate amount of water to the sulfonated polyarylene.

For example, the proton conductive membrane may be produced by a casting method in which the sulfonated polyarylene dissolved in a solvent is flow-cast in the form of film over a substrate. The substrate may be any substrate used in the conventional solution casting processes. Examples include, although not particularly limited to, plastic substrates and metal substrates. Preferably, the substrate is a thermoplastic resin substrate, such as a polyethylene terephthalate (PET) film.

Solvents to dissolve the sulfonated polyarylene include aprotic polar solvents such as N-methyl-2-pyrrolidone, N,N-dimethylformamide, γ-butyrolactone, N,N-dimethylacetamide, dimethyl sulfoxide, dimethylurea and dimethylimidazolidinone. In view of solubilizing ability and solution viscosity, N-methyl-2-pyrrolidone (hereinafter "NMP") is preferred. The aprotic polar solvents may be used singly or in combination of two or more kinds.

The solvent for dissolving the sulfonated polyarylene may be a mixed solvent of the above aprotic polar solvent and an alcohol. Exemplary alcohols include methanol, ethanol, propyl alcohol, isopropyl alcohol, sec-butyl alcohol and tert-butyl alcohol. In particular, methanol is preferable since it ensures an appropriately low solution viscosity over a wide range of the polyarylene proportions. These alcohols may be used either singly or in combination of two or more kinds.

The solution viscosity may vary depending on the molecular weight of the sulfonated polyarylene or the polymer concentration. Generally, it is between 2,000 and 100,000 mPa·s, and preferably between 3,000 and 50,000 mPa·s. When the viscosity is less than 2,000 mPa·s, the solution will have too high a fluidity and may spill out of the substrate during the membrane production. On the contrary, the viscosity over 100,000 mPa·s is so high that the solution cannot be extruded through a die and the flow-casting for the film production may be difficult.

When a solvent of high boiling point is used in the above casting method, a large amount of the solvent may remain in the film obtained as described above. In such a case, the amount of the remaining solvent in the film may be reduced by soaking the wet film into water to substitute the remaining solvent with water.

Soaking the wet films in water may be carried out batchwise with respect to each sheet, or may be a continuous process where the films which may be in the original form of laminate with a substrate film (e.g. PET film) as produced or the films released from the substrate, are soaked and then wound sequentially.

In the batchwise soaking, the films are suitably framed or fixed by similar means to prevent wrinkles from forming on the surface of treated films.

The soaking should be suitably made so that the wet films would contact with water that is at least 10 parts by weight, and preferably 30 parts by weight based on 1 part by weight of the films. This contact ratio is suitably maintained as large as possible to minimize the amount of solvent remaining in the proton conductive membrane. For the purpose of reducing the residual solvent amount, it is also effective to keep the concentration of the organic solvent in water at or below a certain level by renewing the water used in the soaking or by letting the water overflow. The in-plane distribution of the organic solvent in the proton conductive membrane may be effectively reduced by homogenizing the organic solvent concentration in the water by stirring or the like.

The proton conductive membrane obtained by the method of the invention generally has a dry membrane thickness of 10 to 100 μm, and preferably 20 to 80 μm.

The proton conductive membrane comprising the sulfonated polyarylene may be produced in the reversed order to the above procedure. That is, the hydrolysis may be carried out after the polyarylene has been formed into films. In this case too, the hydrolysis may be performed by the method described above.

The aromatic sulfonate derivative and the polyarylene according to the invention may be used in the sulfonated polyarylene and in the production method thereof as described hereinabove.

The proton conductive membrane of the invention has an excellent proton conductivity, particularly at low humidity.

EXAMPLE

The present invention will be hereinafter described in detail by the following Examples, but it should be construed that the invention is in no way limited to those Examples.

In these embodiments, the equivalent amount of sulfonic acid, the molecular weight and the proton conductivity were determined as described below.

1. Equivalent Amount of Sulfonic Acid

The sulfonated polyarylene obtained was washed with water until neutrality was reached in the used wash water. Thereafter, the residual free acids were removed. The sulfonated polyarylene was further washed with water and then dried. A given amount of the sulfonated polyarylene was weighed out and dissolved in a THF/water mixed solvent. The solution thus obtained was titrated using a standard solution of NaOH. In the titration, phenolphthalein was used as an indicator. The equivalent amount of sulfonic acid was obtained by completeness of neutralization..

2. Measurement of Molecular Weight

Prior to the hydrolysis, the weight-average molecular weight of the polyarylene was measured in terms of polystyrene according to GPC using tetrahydrofuran (THF) as a solvent. After the sulfonated polyarylene had been obtained by the hydrolysis, its molecular weight in terms of polystyrene was determined by GPC using, as an eluting solvent, N-methyl-2-pyrrolidone (NMP) mixed with lithium bromide and phosphoric acid.

3. Measurement of Proton Conductivity

A 5 mm-wide strip specimen of the proton conductive membrane, holding 5 platinum wires (diameter: 0.5 mm) on its surface, was placed in a thermo-hygrostat. Then the alternating current impedance between the platinum wires was measured at 85° C. and 10 kHz under a different relative humidity of 95%, 70% or 30%. This measurement was carried out using a chemical impedance measuring system (NF Corporation) and thermo-hygrostat JW241 (Yamato Science Co., Ltd.). The alternating current resistance was measured in each case where the interwire distance was changed from 5 mm to 20 mm among the 5 platinum wires placed at intervals of 5 mm. The resistivity of the membrane was calculated by the following formula from a gradient between the interwire distance and the resistance. The reciprocal number of resistivity was obtained as the alternating current impedance, from which the proton conductivity was calculated.

Resistivity $R(\Omega \cdot cm) = 0.5(cm) \times$ membrane thickness $(cm) \times$ resistance/interwire distance gradient $(\Omega/cm)$

Synthesis Example 1

(Preparation of Oligomer)

Into a 1-liter, three-necked flask equipped with a stirrer, a thermometer, a condenser tube, a Dean-Stark tube and a three-way nitrogen introduction cock were charged:

67.3 g (0.20 mol) of 2,2-bis(4-hydroxyphenyl)-1,1,1,3,3,3-hexafluoropropane (bisphenol AF), 60.3 g (0.24 mol) of 4,4'-dichlorobenzophenone (4,4'-DCBP), 71.9 g (0.52 mol) of potassium carbonate, 300 ml of N,N-dimethylacetamide (DMAc), and 150 ml of toluene.

The flask was placed in an oil bath, and the contents were heated at 130° C. with stirring in a nitrogen atmosphere. Water yielded during the reaction was allowed to form an azeotropic mixture with toluene and removed outside the system through the Dean-Stark tube. The generation of water almost ceased in about 3 hours. Then the reaction temperature was raised gradually from 130° C. to 150° C., during which most of the toluene was removed. After the reaction was continued at 150° C. for 10 hours, 10.0 g (0.040 mole) of 4,4'-DCBP was added and the reaction was continued for another 5 hours. The reaction solution thus obtained was allowed to cool naturally and filtered to remove the precipitate consisting of by-product inorganic compounds. The filtrate was poured into 4 liters of methanol. The precipitated reaction product was recovered by filtration, dried and dissolved in 300 ml of tetrahydrofuran. The thus-formed solution was poured into 4 liters of methanol to precipitate the objective compound. The compound weighed 95 g (85% yield).

The polymer had a weight-average molecular weight in terms of polystyrene of 12,500 as measured by the GPC (THF solvent). The polymer was found to be soluble in THF, NMP, DMAc, sulfolane and the like. The glass transition temperature (Tg) and heat decomposition temperature were 110° C. and 498° C. respectively.

The compound obtained above was an oligomer represented by the following formula (I) (hereinafter the "BCPAF oligomer"):

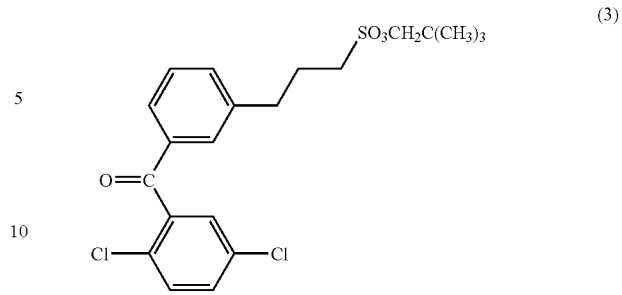

The reactants were heated with stirring (the system temperature was finally increased up to 74° C.) and reacted for 3 hours. The viscosity of the reaction system was confirmed to increase in the course of the reaction. The polymerization solution was then diluted with 250 ml of THF, stirred for 30 minutes, and filtered with use of Celite as a filter aid. Pouring the filtrate into a large excess of methanol (1500 ml) caused solids. These solids were filtered off, air dried, and redissolved in a THF/NMP (200/30 ml) solvent. The resultant solution was poured into a large excess of methanol (1500 ml) to precipitate solids, which were collected and dried by blowing air and thereafter by heating. As a result, an objective, yellow flake copolymer was obtained that comprised a sulfonic acid derivative having neopentyl protective groups. The copolymer weighed 20.54 g (78% yield). The GPC molecular weights were Mn=52,600 and Mw=174,300.

Of the copolymer comprising a sulfonic acid derivative with neopentyl protective groups, a 10 g portion was gradually added to 60 ml of trifluoroacetic acid. The resultant viscous solution was heated until a reflux was caused, when 10 ml of trifluoroacetic acid was further added. The reaction was continued with stirring for 5 hours in total. The reaction solution was cooled to room temperature, and the formed precipitate was filtered off. The product was then suspended in 500 ml of THF with stirring, washed, filtered off, and dried in vacuo to obtain a crude composition. The crude composition was washed with water three times, and was obtained as polymer powder.

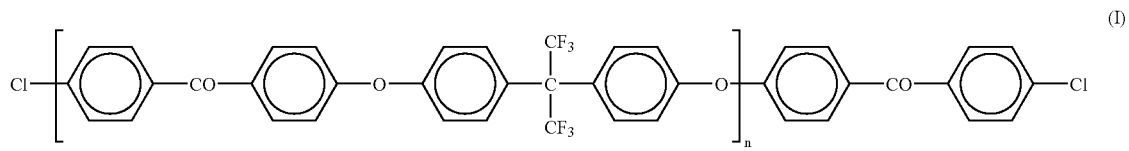

(Polymerization of Polyarylene)

Example 1

In an atmosphere of nitrogen, 60 ml of dried N-methylpyrrolidone (NMP) was added to a mixture consisting of:

14.50 g (32.7 mmol) of a compound represented by the following formula (3), 5.00 g (0.63 mmol) of the BCPAF oligomer (Mn=7,940), 0.65 g (1 mmol) of Ni(PPh$_3$)$_2$Cl$_2$, 33.50 g (13.33 mmol) of PPh, 0.65 g (4.83 mmol) of NaI, and 5.45 g (83.33 mmol) of zinc powder.

A 8-wt % NMP solution of the polymer was cast over a glass plate to form a coating. The coating was dried with air and in vacuo, thereby obtaining a 40 μm thick film. The IR spectrum and the results of the quantitative analysis of ion exchange capacity of the film proved that the sulfonate groups had been quantitatively converted to sulfonic groups.

The polymer had a sulfonic group content of 1.9 meq/g (which was identical with the theoretical value 1.9 meq/g calculated from the mol of the monomers used in the polymerization).

The film of the sulfonic acid polymer had the proton conductivities of:

0.232 S/cm at 85° C. and 95% RH, 0.098 S/cm at 85° C. and 70% RH, and 0.021 S/cm at 85° C. and 30% RH.

EFFECT OF THE INVENTION

The production method of sulfonated polyarylene according to the invention involves no sulfonating agents for the introduction of sulfonic groups into the polyarylene. Thus, the sulfonated polyarylene may be produced safely. Further, the invention enables least work for the post-production treatment after the polymer has been recovered. It is also possible by the invention to control the amount and position of introduced sulfonic groups in the polymer.

The aromatic sulfonate derivative and the polyarylene according to the invention may be used for the sulfonated polyarylene and in the production thereof.

The proton conductive membrane of the invention has an excellent proton conductivity.

The invention claimed is:

1. A macromolecular solid electrolyte comprising a sulfonated polyarylene obtained by hydrolysis of a polyarylene comprising structural units derived from an aromatic compound, wherein at least part of the structural units are represented by the formula (1'):

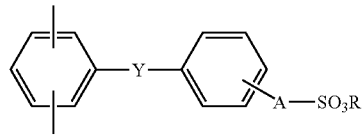

(1')

wherein Y is a divalent organic group; A is —$(CH_2)_m$— or —$(CF_2)_m$— (wherein m is an integer of 1 to 10); and R is a $C_{4-20}$ hydrocarbon group.

2. The macromolecular solid electrolyte of claim 1 wherein the sulfonated polyarylene comprises 0.5–100 mol % structural units represented by the formula (1') and 0–99.5 mol % structural units represented by the following formula (A'):

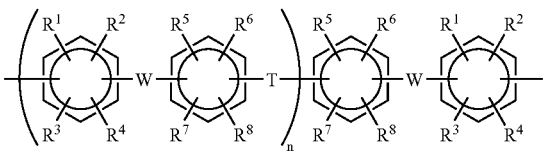

(A')

wherein $R_1$ to $R_8$, which may be the same or different, are independently at least one atom or group selected from the group consisting of a hydrogen atom, a fluorine atom, and alkyl, fluorine-substituted alkyl, allyl and aryl groups; W is a divalent electron-attracting group; and T is a divalent organic group.

3. A proton conductive membrane for fuel cells that contains the macromolecular solid electrolyte of claims 1 or 2.

* * * * *